United States Patent [19]
Fischer et al.

[11] 3,947,485

[45] Mar. 30, 1976

[54] CARBOTHIOLATES

[75] Inventors: Adolf Fischer, Mutterstadt;
Karl-Heinz Koenig, Frankenthal;
Rudolf Kolbinger, Speyer, all of Germany

[73] Assignee: BASF Aktiengesellschaft, Ludwigshafen (Rhine), Germany

[22] Filed: May 31, 1974

[21] Appl. No.: 474,900

[30] Foreign Application Priority Data
June 7, 1973 Germany............................ 2329043

[52] U.S. Cl.............................. 260/455 A; 71/100
[51] Int. Cl.²........................................ C07C 155/02
[58] Field of Search................................ 260/455 A

[56] References Cited
UNITED STATES PATENTS

| | | | |
|---|---|---|---|
| 2,901,498 | 8/1959 | Tilles et al. | 260/455 A |
| 2,901,499 | 8/1959 | Tilles et al. | 260/455 A |
| 2,916,369 | 12/1959 | Tilles et al. | 260/455 A |
| 2,916,370 | 12/1959 | Tilles et al. | 260/455 A |
| 3,224,863 | 12/1965 | D'Amico | 260/455 A |
| 3,264,339 | 8/1966 | Swakon | 260/455 A |

FOREIGN PATENTS OR APPLICATIONS

| | | | |
|---|---|---|---|
| 3,911,213 | 8/1961 | Japan | 260/455 A |

*Primary Examiner*—Lewis Gotts
*Assistant Examiner*—D. R. Phillips
*Attorney, Agent, or Firm*—Johnston, Keil, Thompson & Shurtleff

[57] ABSTRACT

New and valuable N-cycloalkyl-, N-alkenyl- or alkynyl-substituted carbothiolates having a good herbicidal action, herbicides containing these compounds, a process for controlling the growth of unwanted plants with these compounds, and a process for producing these compounds.

4 Claims, No Drawings

CARBOTHIOLATES

The present invention relates to new and valuable N-cycloalkyl-, N-alkenyl- and alkynyl-substituted carbothiolates, herbicides containing them, and the use of these compounds as herbicides.

It is known (British patent No. 995,316) to use S-ethyl-N-ethyl-N-cyclohexyl carbothiolates for controlling unwanted plants in crops such as beet, spinach and Indian corn. However, its action is poor.

We have now found that carbothiolates of the formula

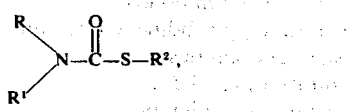

where R denotes a monocycloaliphatic or bicycloaliphatic radical of 5 to 8 carbon atoms, $R^1$ denotes propenyl or butenyl, and $R^2$ denotes lower alkyl of 2 to 4 carbon atoms or an aliphatic-aromatic radical which may be substituted in the p-position by halogen, and $R^1$ additionally denotes a propargyl or butyn-(2)-yl-(4) radical when R is norbornyl, have a better herbicidal action than the prior art active ingredients. The compounds of the invention have a better crop plant compatibility and a better herbicidal action on unwanted plants than S-ethyl-N-ethyl-N-cyclohexyl carbothiolate.

The compounds may be prepared by reacting a thiol chloroformate with an alkenyl- or alkynyl-substituted monocycloaliphatic or bicycloaliphatic amine. The secondary amines can be prepared by alkylation of cycloaliphatic amines with the appropriate propenyl, butenyl and butynyl halides.

EXAMPLE 1

Preparation of N-cyclohexyl-N-propenylamino-S-ethyl carbothiolate

At 60° to 70°C, 23.2 parts (by weight) of thioethyl chloroformate is dripped into 26 parts of cyclohexylallylamine and 20 parts of triethylamine in 250 parts of benzene. The mixture is stirred for 7 hours at 60° to 70°C and cooled; 250 parts of water is added and the organic phase separated. The solvent is distilled under a water jet vacuum and the residue under an oil pump vacuum. The yield is 24 parts of the desired product; boiling point (0.1 mm): 117°C.

The following carbothiolates were obtained in the same manner:

| | | | |
|---|---|---|---|
| N-norbornyl-N-allylamino-S-benzyl carbothiolate | b.p. | (0.04 mm) | 180°C |
| N-norbornyl-N-propargylamino-S-propyl carbothiolate | b.p. | (0.002) | 133°C |
| N-norbornyl-N-propargylamino-S-benzylcarbothiolate | b.p. | (0.02) | 180°C |
| N-norbornyl-N-butyn-(2)-yl-(1)-amino-S-benzyl carbothiolate | b.p. | (1.3) | 210°C |
| N-cyclohexyl-N-allylamino-S-benzyl carbothiolate | b.p. | (0.3) | 164°C |
| N-norbornyl-N-butyn-(2)-yl-(1)-amino-S-(p-chlorobenzyl)-carbothiolate | b.p. | (0.04) | 200°C |
| N-cyclohexyl-N-allylamino-S-n-propyl carbothiolate | b.p. | (0.4) | 113–6°C |
| N-norbornyl-N-butyn-(2)-yl-(1)-amino-S-n-propyl carbothiolate | b.p. | (0.2) | 132–4°C |
| N-norbornyl-N-allylamino-S-ethyl carbothiolate | b.p. | (0.1) | 117°C |
| N-norbornyl-N-propargylamino-S-ethyl carbothiolate | b.p. | (0.6) | 120–4°C |
| N-norbornyl-N-butyn-(2)-yl-(1)-amino-S-ethyl carbothiolate | b.p. | (0.5) | 152°C |
| N-cyclohexyl-N-allylamino-S-ethyl carbothiolate | b.p. | (0.1) | 117°C |
| N-norbornyl-N-allylamino-S-n-propyl carbothiolate | b.p. | (0.05) | 117°C |
| N-cyclohexyl-N-allylamino-S-ethyl-(p-chlorobenzyl)-carbothiolate | b.p. | (0.01) | 173–5°C |
| N-norbornyl-N-allylamino-S-(p-chlorobenzyl)-carbothiolate | b.p. | (0.04) | 200°C |
| N-norbornyl-N-propargylamino-S-(p-chlorobenzyl)-carbothiolate | b.p. | (0.01) | 215°C |

Application may be effected for instance in the form of directly sprayable solutions, powders, suspensions, dispersions, emulsions, oil dispersions, pastes, dusts, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral fractions of medium to high boiling point, such as kerosene or diesel oil, further coal-tar oils and oils of vegetable or mineral origin, aliphatic, cyclic and aromatic hydrocarbons such as benzene, toluene, xylene, paraffin, tetrahydronaphthalene, alkylated naphthalenes, methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts or ligninsulfonic acid, naphthalenesulfonic acid, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, broadcasting agents and dusts may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The compositions contain from 0.1 to 95, and preferably from 0.5 to 90, % of active ingredient.

There may be added (if desired, immediately before use) to the compositions or individual active ingredients oils of various types, herbicides, fungicides, nematocides, insecticides, bactericides, trace elements, fertilizers, antifoams (e.g., silicones), growth regulators, antidotes and other herbicidally effective compounds such as substituted anilines,
substituted aryloxycarboxylic acids and salts, esters and amides thereof,
substituted ethers,
substituted arsonic acids and their salts, esters and amides,
substituted benzimidazoles,
substituted benzisothiazoles,
substituted benzothiadiazinone dioxides,
substituted benzoxazines, substituted benzoxazinones,
substituted benzothiadiazoles,
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkylthiol- or -dithiophosphates,
substituted quinazolines,
substituted cycloalkylamidocarbothiolic acids and their salts, esters, and amides,
substituted cycloalkylcarbonamidothiazoles,
substituted dicarboxylic acids and their salts, esters and amides,
substituted dihydrobenzofuranyl sulfonates,
substituted disulfides,
substituted dipyridylium salts,
substituted dithiocarbamates,
substituted dithiophosphoric acids and their salts, esters and amides,
substituted ureas,
substituted hexahydro-1H-carbothioates,
substituted hydantoins,
substituted hydrazides,
substituted hydrazonium salts,
substituted isooxazole pyrimidones,
substituted imidazoles,
substituted isothiazole pyrimidones,
substituted ketones,
substituted naphthoquinones,
substituted aliphatic nitriles,
substituted aromatic nitriles,
substituted oxadiazoles,
substituted oxadiazinones,
substituted oxadiazolidine diones,
substituted oxadiazine diones,
substituted phenols and their salts and esters,
substituted phosphoric acids and their salts, esters and amides,
substituted phosphonium chlorides,
substituted phosphonalkylglycines,
substituted phosphites,
substituted phosphoric acids and their salts, esters and amides,
substituted piperidines,
substituted pyrazoles,
substituted pyrazole alkylcarboxylic acids and their salts, esters and amides,
substituted pyrazolium salts,
substituted pyrazolium alkyl sulfates,
substituted pyridazines,
substituted pyridazones,
substituted pyridine carboxylic acids and their salts, esters and amides,
substituted pyridines,
substituted pyridine carboxylates,
substituted pyridinones,
substituted pyrimidines,
substituted pyrimidones,
substituted pyrrolidine carboxylic acid and its salts, esters and amides,
substituted pyrrolidines,
substituted pyrrolidones,
substituted arylsulfonic acids and their salts, esters and amides,
substituted styrenes,
substituted tetrahydrooxadiazine diones,
substituted tetrahydrooxadiazole diones,
substituted tetrahydromethanoindenes,
substituted tetrahydrooxadiazole thiones,
substituted tetrahydrodiazine thiones,
substituted tetrahydrothiadiazole diones,
substituted aromatic thiocarbonylamides,
substituted thiocarboxylic acids and their salts, esters and amides,
substituted thiol carbamates,
substituted thioureas,
substituted thiophosphoric acids and their salts, esters and amides,
substituted triazines,
substituted uracils,
substituted uretidine diones.

These herbicidal compounds may be applied before or after the compounds of the invention.

These agents may be added to the herbicides according to the invention in a ratio by weight of from 1:10 to 10:1. The same applies to oils, fungicides, nematocides, insecticides, bactericides, antidotes and growth regulators.

The agents according to the invention may be applied once or several times before or after planting, before sowing, pre- or postemergence, or during emergence of the crop plants or weeds.

The agents have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance

| | |
|---|---|
| *Gramineae*, such as | |
| *Cynodon* spp. | *Dactylis* spp. |
| *Digitaria* spp. | *Avena* spp. |
| *Echinochloa* spp. | *Bromus* spp. |
| *Setaria* spp. | *Uniola* spp. |
| *Panicum* spp. | *Poa* spp. |
| *Alopecurus* spp. | *Leptochloa* spp. |
| *Lolium* spp. | *Brachiaria* spp. |
| *Sorghum* spp. | *Eleusine* spp. |
| *Agropyron* spp. | *Cenchrus* spp. |
| *Phalaris* spp. | *Eragrostis* spp. |
| *Apera* spp. | etc.; |
| *Cyperaceae*, such as | |
| *Carex* spp. | *Eleocharis* spp. |
| *Cyperus* spp. | etc.; |
| *Scirpus* spp. | |
| dicotyledonous weeds, such as | |
| *Malvaceae*, e.g. | |
| *Abutilon theoprasti* | *Hibiscus* spp. |
| *Sida* spp. | *Malva* spp. |
| etc.; | |
| *Compositae*, such as | |
| *Ambrosia* spp. | *Centaurea* spp. |
| *Lactuca* spp. | *Tussilago* spp. |
| *Senecio* spp. | *Lapsana communis* |
| *Sonchus* spp. | *Tagetes* spp. |
| *Xanthium* spp. | *Erigeron* spp. |
| *Iva* spp. | *Anthemis* spp. |
| *Galinsoga* spp. | *Matricaria* spp. |
| *Taraxacum* spp. | *Artemisia* spp. |
| *Chrysanthemum* spp. | *Bidens* spp. |
| *Cirisum* spp. | etc.; |
| *Convolvulaceae*, such as | |
| *Convolvulus* spp. | *Cuscuta* spp. |
| *Ipomoea* spp. | *Jaquemontia tamnifolia* |
| etc.; | |
| *Cruciferae*, such as | |
| *Barbarea vulgaris* | *Arabidopsis thaliana* |
| *Brassica* spp. | *Descurainia* spp. |
| *Capsella* spp. | *Draba* spp. |
| *Sisymbrium* spp. | *Coronopus didymus* |
| *Thlaspi* spp. | *Lepidium* spp. |
| *Sinapis arvensis* | *Raphanus* spp. |
| etc.; | |
| *Geraniaceae*, such as | |
| *Erodium* spp. | *Geranium* spp. |
| etc.; | |
| *Portulacaceae*, such as | |
| *Portulaca* spp. | etc.; |
| *Primulaceae*, such as | |
| *Anagallis arvensis* | *Lysimachia* spp. |
| etc.; | |
| *Rubiaceae*, such as | |
| *Richardia* spp. | *Diodia* spp. |
| *Galium* spp. | etc.; |
| *Scrophulariaceae*, such as | |
| *Linaria* spp. | *Digitalis* spp. |
| *Veronica* spp. | etc.; |
| *Solanaceae*, such as | |
| *Physalis* spp. | *Nicandra* spp. |
| *Solanum* spp. | *Datura* spp. |
| etc.; | |
| *Urticaceae*, such as | |
| *Urtica* spp. | etc.; |
| *Violaceae*, such as | |
| *Viola* spp. | etc.; |
| *Zygophyllaceae*, such as | |
| *Tribulus terrestis* | etc.; |
| *Euphorbiaceae*, such as | |
| *Mercurialis annua* | *Euphorbia* spp. |
| *Umbelliferae*, such as | |
| *Daucus carota* | *Ammi majus* |
| *Aethusa cynapium* | etc.; |
| *Commelinaeae*, such as | |
| *Commelina* spp. | etc.; |
| *Labiatae*, such as | |
| *Lamium* spp. | *Galeopsis* spp. |
| etc.; | |
| *Leguminosae*, such as | |
| *Medicago* spp. | *Sesbania exaltata* |
| *Trifolium* spp. | *Cassia* spp. |
| *Vicia* spp. | *Lathyrus* spp. |
| etc.; | |
| *Plantaginaceae*, such as | |
| *Plantago* spp. | etc.; |
| *Polygonaceae*, such as | |
| *Polygonum* spp. | *Fagopyrum* spp. |
| *Rumex* spp. | etc.; |
| *Aizoaceae*, such as | |
| *Mollugo verticillata* | etc.; |
| *Amaranthaceae*; such as | |
| *Amaranthus* spp. | etc.; |
| *Boraginaceae*, such as | |
| *Amsinckia* spp. | *Anchusa* spp. |
| *Myostis* spp. | *Lithospermum* spp. |
| etc.; | |
| *Caryophyllaceae*, such as | |
| *Stellaria* spp. | *Silene* spp. |
| *Spergula* spp. | *Cerastium* spp. |
| *Saponaria* spp. | *Agrostemma githago* |
| *Scleranthus annuus* | etc.; |
| *Chenopodiaceae*, such as | |
| *Chenopodium* spp. | *Atriplex* spp. |
| *Kochia* spp. | *Monolepsis nuttaliana* |
| *Salsola kali* | etc.; |
| *Lythraceae*, such as | |
| *Cuphea* spp. | etc.; |
| *Oxalidaceae*, such as | |
| *Oxalis* spp. | etc.; |
| *Ranunculaceae*, such as | |
| *Ranunculus* spp. | *Adonis* spp. |
| *Delphinium* spp. | etc.; |
| *Papaveraceae*, such as | |
| *Papaver* spp. | *Fumaria officinalis* |
| etc.; | |
| *Onagraceae*, such as | |
| *Jussiaea* spp. | etc.; |
| *Rosaceae*, such as | |
| *Alchemillia* spp. | *Potentilla* spp. |
| etc.; | |
| *Potamogetonaceae*, such as | |
| *Potamogeton* spp. | etc.; |
| *Najadeceae*, such as | |
| *Najas* spp. | etc.; |
| *Marsileaceae*, such as | |
| *Marsilea quadrifolia* | etc.; |

The new agents may be employed in crops such as

| | |
|---|---|
| *Avena* spp. | *Sorghum* |
| *Triticum* spp. | *Zea mays* |
| *Hordeum* spp. | *Panicum miliaceum* |
| *Secale* spp. | *Oryza* spp. | and in *dicotyledon* crops such as

| | |
|---|---|
| *Cruciferae*, such as | |
| *Brassica* spp. | *Raphanus* spp. |
| *Sinapis* spp. | *Lepidium* spp. |
| *Compositae*, such as | |
| *Lactuca* spp. | *Carthamus* spp. |
| *Helianthus* spp. | *Scorzonera* spp. |
| *Malvaceae*, such as | |
| *Gossypium hirsutum* | |
| *Leguminosae*, such as | |
| *Medicago* spp. | *Phaseolus* spp. |
| *Trifolium* spp. | *Arachis* spp. |
| *Pisum* spp. | *Glycine max.* |
| *Chenopodiacea*, such as | |
| *Beta vulgaris* | |
| *Spinacia* spp. | |
| *Solanaceae*, such as | |
| *Solanum* spp. | *Capsicum annuum* |
| *Nicotiania* spp. | |
| *Linaceae*, such as | |
| *Linum* spp. | |
| *Umbelliferae*, such as | |
| *Petroselinum* spp. | *Apium graveolens* |
| *Daucus carota* | |
| *Rosaceae*, such as | *Fragaria* |
| *Cucurbitaceae*, such as | |
| *Cucumis* spp. | *Cucurbita* spp. |
| *Liliaceae*, such as | |
| *Allium* spp. | |
| *Vitaceae*, such as | |
| *Vitis vinifera* | |
| *Bromeliaceae*, such as | |
| *Ananas sativus* | |

The amount used of the agents of the invention may vary and depends on the effect desired; it generally is from 0.1 to 15 and more, and preferably 0.2 to 6, kg per hectare.

The compositions may also be used as total agents in ditches, on aquatic areas, railway tracks, barren and waste land, etc.

EXAMPLE 2

In the greenhouse, loamy sandy soil was filled into pots and sown with the seeds of various plants. The soil prepared in this manner was then immediately treated with 1 kg per hectare of each of the following active ingredients, each being dispersed or emulsified in 500 liters of water per hectare:

I. N-cyclohexyl-N-allylamino-S-ethyl carbothiolate
II. N-norbornyl-N-allylamino-S-ethyl carbothiolate
and, for comparison,
III. ethyl N-ethyl-N-cyclohexylthiol carbamate.

After 3 to 4 weeks it was ascertained that active ingredients I and II had a better herbicidal action than compound III, combined with superior crop plant compatibility.

The results are given below:

| Active ingredient kg/ha | I 1 | II 1 | III 1 |
|---|---|---|---|
| Crop plants: | | | |
| Beta vulgaris | 0 | 0 | 10 |
| Spinacia oleracea | 0 | 0 | 10 |
| Zea mays | 0 | 0 | 20 |
| Unwanted plants: | | | |
| Avena fatua | 60 | 50 | 36 |
| Lolium multiflorum | 85 | 88 | 40 |
| Lolium perenne | 60 | 50 | 40 |
| Bromus tectorum | 70 | 45 | 35 |
| Poa annua | 70 | 50 | 40 |
| Apera spica venti | 72 | 60 | 35 |
| Festuca rubra | 60 | 55 | 43 |
| Echinochloa crus-galli | 75 | 60 | 40 |
| Digitaria sanguinalis | 70 | 70 | 40 |
| Eleusine indica | 72 | 60 | 42 |
| Panicum virgatum | 75 | 60 | 45 |
| Alopecurus myosuroides | 70 | 70 | 60 |
| 0 = no damage | | | |
| 100 = complete destruction | | | |

EXAMPLE 3

In the greenhouse, various plants were treated at a growth height of from 3 to 11 cm with 1 kg per hectare of each of the following compounds, each being dispersed or emulsified in 500 liters of water per hectare:

I. N-cyclohexyl-N-allylamino-S-ethyl carbothiolate
II. N-norbornyl-N-allylamino-S-ethyl carbothiolate
and, for comparison,
III. ethyl N-ethyl-N-cyclohexylthiol carbamate.

After 3 to 4 weeks it was ascertained that active ingredients I and II had a better herbicidal action than compound III, combined with superior crop plant compatibility.

The results are given below:

| Active ingredient kg/ha | I 1 | II 1 | III 1 |
|---|---|---|---|
| Crop plants: | | | |
| Beta vulgaris | 0 | 2 | 5 |
| Spinacia oleracea | 0 | 1 | 4 |
| Zea mays | 0 | 0 | 0 |

-continued

| Active ingredient kg/ha | I 1 | II 1 | III 1 |
|---|---|---|---|
| Unwanted plants: | | | |
| Avena fatua | 60 | 65 | 10 |
| Alopecurus myosuroides | 40 | 60 | 15 |
| Echinochloa crus galli | 60 | 35 | 12 |
| Lolium multiflorum | 75 | 80 | 20 |
| 0 = no damage | | | |
| 100 = complete destruction | | | |

EXAMPLE 4

In the greenhouse, loamy sandy soil was filled into pots and sown with the seeds of various plants. The soil prepared in this manner was then immediately treated with 1 kg per hectare of each of the following active ingredients, each dispersed or emulsified in 500 liters of water per hectare:

I. N-cyclohexyl-N-allylamino-S-ethyl carbothiolate
II. N-norbornyl-N-allylamino-S-ethyl carbothiolate
and, for comparison,
III. N-cyclohexyl-N-propargyl-S-ethyl carbothiolate
IV. N-tricyclo-[5,2,1,0,2,6]-decyl-S-ethyl carbothiolate.

After 3 to 4 weeks it was ascertained that active ingredients I and II had a better herbicidal action than compounds III and IV, combined with the same good crop plant compatibility.

The results are given below:

| Active ingredient kg/ha | I 1 | II 1 | III 1 | IV 1 |
|---|---|---|---|---|
| Crop plants: | | | | |
| Beta vulgaris | 0 | 0 | 0 | 0 |
| Spinacia oleracea | 0 | 0 | 0 | 0 |
| Zea mays | 0 | 0 | 0 | 0 |
| Unwanted plants: | | | | |
| Lolium multiflorum | 85 | 88 | 35 | 55 |
| Bromus tectorum | 70 | 45 | 30 | 38 |
| Echinochloa crus galli | 75 | 60 | 37 | 50 |
| Eleusine indica | 72 | 60 | 50 | 53 |
| Alopecurus myosuroides | 70 | 70 | 54 | 58 |
| 0 = no damage | | | | |
| 100 = complete destruction | | | | |

EXAMPLE 5

90 parts by weight of compound I is mixed with 10 parts by weight of N-methyl-α-pyrrolidone. A mixture is obtained which is suitable for application in the form of very fine drops.

EXAMPLE 6

20 parts by weight of compound II is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound I is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound II is dissolved in a mixture consisting of 25 parts by weight of cyclohexanol, 65 parts by weight of a mineral oil fraction having a boiling point between 210° and 280°C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound I is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 10

3 parts by weight of compound II is intimately mixed with 97 parts by weight of particulate kaolin. A dust is obtained containing 3% by weight of the active ingredient.

EXAMPLE 11

30 parts by weight of compound I is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:

1. A carbothiolate of the formula $$\begin{array}{c} R \\ \phantom{R}\diagdown \\ \phantom{RR}N-\underset{\underset{\displaystyle\|}{O}}{C}-S-R^2, \\ \phantom{RR}\diagup \\ R^1 \end{array}$$

where R denotes a monocycloaliphatic or bicycloaliphatic radical of 5 to 8 carbon atoms, $R^1$ denotes propenyl or butenyl, $R^2$ denotes lower alkyl of 2 to 4 carbon atoms or a benzyl radical which may be substituted in the p-position by halogen, and $R^1$ additionally denotes a propargyl or butyn-(2)-yl-(4) radical when R is norbornyl.

2. N-cyclohexyl-N-allylamino-S-ethyl carbothiolate.

3. N-cyclohexyl-N-allylamino-S-n-propyl carbothiolate.

4. N-norbornyl-N-allylamino-S-ethyl carbothiolate.

* * * * *